United States Patent [19]

Gergely et al.

[11] Patent Number: 4,867,942

[45] Date of Patent: Sep. 19, 1989

[54] PROCESS FOR THE PREPARATION OF AN EFFERVESCENT GRANULAR MATERIAL, EFFERVESCENT GRANULAR MATERIAL PREPARED BY THIS PROCESS, AS WELL AS THE USE THEREOF

[76] Inventors: Gerhard Gergely; Irmgard Gergely; Stefan M. Gergely; Thomas Gergely, all of Gartengasse 8, A-1050 Wien, Austria

[21] Appl. No.: 251,060

[22] Filed: Sep. 27, 1988

Related U.S. Application Data

[63] Continuation of Ser. No. 919,457, Oct. 16, 1986, abandoned.

[30] Foreign Application Priority Data

Jun. 26, 1986 [DE] Fed. Rep. of Germany ....... 3621432
Aug. 13, 1986 [DE] Fed. Rep. of Germany ....... 3627475

[51] Int. Cl.$^4$ .............................................. A61K 9/46
[52] U.S. Cl. .................................... 424/466; 421/481
[58] Field of Search ........................... 424/489, 466, 44

[56] References Cited

U.S. PATENT DOCUMENTS

| | | | |
|---|---|---|---|
| 4,036,228 | 7/1977 | Theunoves | 424/466 |
| 4,127,645 | 11/1978 | Wetzel et al. | 424/466 |
| 4,678,661 | 7/1987 | Gergely et al. | 424/44 |

Primary Examiner—Thurman K. Page
Assistant Examiner—Leon R. Horne
Attorney, Agent, or Firm—Hill, Van Santen, Steadman & Simpson

[57] ABSTRACT

Process for the preparation of an effervescent granular material containing at least one solid, crystalline, edible organic acid, particularly citric acid and at least one alkali metal or alkaline earth metal carbonate splitting off $CO_2$ on reacting with the organic acid in aqueous solution, in which optionally in a vacuum mixing machine, the acid crystals are wetted in a first reaction stage with a solvent for the acid, such as water, alcohol or a mixture thereof and are then thoroughly mixed for forming a first coating with a first pulverized coating compound containing at least one alkali metal or alkaline earth metal carbonate adhering to a binding coating formed by the reaction of acid and carbonate on the surface coating of the particular acid crystal, after which following formation of the first coating in at least one further reaction stage at least one further solid, pulverized coating compound, optionally coinciding with the first and having a content of at least one alkali metal or alkaline earth metal carbonate is added and reacted under vigorous stirring on the preceding coating formed during the preceding reaction stage and moist through the water of crystallization split off during the reaction and finally final drying takes place after breaking off coating formation, wherein part of the total acid quantity and part of the alkali metal and/or alkaline earth metal carbonate of the first coating compound is dissolved in the solvent prior to the appplication thereof to the acid crystals and they are reacted together, the thus prepared prereaction solution then being applied to the acid crystals, the effervescent granular material prepared according to this process and the use thereof.

21 Claims, No Drawings

PROCESS FOR THE PREPARATION OF AN EFFERVESCENT GRANULAR MATERIAL, EFFERVESCENT GRANULAR MATERIAL PREPARED BY THIS PROCESS, AS WELL AS THE USE THEREOF

This is a continuation of application Ser. No. 919,457, filed Oct. 16, 1986, now abandoned.

BACKGROUND OF THE INVENTION

The invention relates to a process for the preparation of an effervescent granular material containing at least one solid, crystalline, edible organic acid, particularly citric acid, to an effervescent granular material prepared by this process, as well as to the use thereof.

DESCRIPTION OF THE PRIOR ART DE-OS 34 34 774 discloses an effervescent granular material of the aforementioned type and a process for the preparation thereof, in which organic acid crystals, particularly citric acid crystals, are provided with a multicoating calcium carbonate-containing covering by reacting in vacuo. The known effervescent granular material has proved very satisfactory in practice, but it has proved desirable to improve the process used for the preparation thereof and which is performed in the prior art in a vacuum mixing machine, so that optionally without any use of a vacuum mixing machine it is possible to prepare effervescent granular materials or granules with the desired quality. However, when using the known vacuum mixing machine improvements are to be obtained with respect to a faster performance of the process and as regards the stability of the effervescent granular materials prepared, particularly if the latter contain very reactive alkali metal or alkaline earth metal carbonates or the latter are present in very high concentration, because in such cases and under given conditions difficulties can arise as a result of excessively violent reactions in the vacuum mixing machine when using the known process of the aforementioned type. Thus, if too much carbonate is reacted with the organic acid in the vacuum mixing machine in a particular process stage and/or too much solution is used, there is an undesired and excessive agglomeration within the vacuum mixing machine boiler or tank, so that lump formation takes place and the stirrer in the tank can be blocked. Thus, the desired objective of reliably coating the acid crystal particles with the carbonate-containing coatings cannot be achieved.

SUMMARY OF THE INVENTION

The problem of the present invention is to so improve the aforementioned process that optionally without using a vacuum mixing machine effervescent granular materials of high quality and stability can be prepared and whilst also permitting a faster performance of the process, even in the case of violently reacting substance combinations for the acid crystals on the one hand and the coatings on the other.

The invention is based on the surprising finding that it is possible to bring about the desired reaction of single or multiple alkali metal or alkaline earth metal carbonate-containing coatings, e.g. on citric acid crystals, optionally without using a vacuum mixing process, such as is e.g. described in Austrian patent 37 61 47 if, prior to the application to the acid crystals, part of the e.g. citric acid and the e.g. calcium carbonate are reacted together in a corresponding solvent, i.e. in water, alcohol or in an alcohol-water mixture and the thus prepared prereaction solution is then applied to the acid crystals. This constitutes an unexpectedly advantageous further development of the procedure known e.g. from DE-OS 34 34 774, according to which reactions with alkali metal or alkaline earth metal bicarbonates or also carbonates can be performed with more or less polar solvents on the surface of the e.g. citric acid crystals and the resulting reaction products and which in the present case essentially consist of mono-salts or optionally di-salts of citric acid, are used as binders for the in each case next coatings or for the incorporation of salts or the like. The problems connected with the known procedure, even when using vacuum mixing processes can be completely avoided as a result of the inventive teaching, in that it is no longer possible for the difficulty to occur that in the case of excessively violent reactions, i.e. on incorporating too much liquid into the vacuum mixing machine, there is an undesired, excessive agglomeration in the interior of the tank, which then leads to lump formation and can also lead to the stirrer in the tank being blocked, so that it is not possible to completely achieve the desired objective of coating the acid crystals. Thus, according to the invention at least part of this reaction is performed outside the tank, in that e.g. both in the case of calcium products and in the case of potassium products citric acid is reacted with calcium carbonate or potassium bicarbonate in such a concentrated form that the finally concentrated solution is clear and at least for a certain time no crystallization takes place. This very concentrated prereaction solution is then sucked into the vacuum mixing machine and has the advantage of initiating no reaction or only a very slight reaction with the acid crystals therein, depending on whether a calcium monocitrate or a calcium dicitrate, in the present example, is prepared in solution. The preparation of a calcium tricitrate solution is not possible, because it is insoluble in water. Thus, if suction of citric acid takes place at the start of a first reaction stage or in further reaction stages with an already prereacted solution, namely the prereaction solution of the reactants used according to the invention instead of with a solvent alone, said solution is eminently suitable to serve as a binder for further calcium carbonate, potassium bicarbonate or sodium bicarbonate coatings. Following the preparation of the corresponding coatings, it can be advantageous to add relatively large quantities of alcohol, preferably isopropanol. These alcohols then precipitate the inorganic salts of the organic acid, particularly citric acid and substantially in anhydrous form, because in the presence of alcohol crystallization with the incorporation of water of crystallization is not possible. Before this alcohol evaporates, it is possible to introduce e.g. starch or also neutral salts, such as calcium lactate or the like and to so to speak "stick on" said salts and then all the water present is removed with the alcohol as the carrier. This process is particularly advantageous, because the very concentrated solutions of in particular potassium citrates only have a very limited vapour pressure, i.e. such a solution would no longer boil at 100° C. and would instead boil at 150° C. or even 180° C., so that evaporation in vacuo at e.g. 70° C. is not readily possible. However, if a precipitation of salts is brought about, accompanied by the addition of alcohol in the manner proposed by the invention and the water present is simultaneously dissolved in the alcohol, then once again normal vapour pressure conditions occur, so that with reduced pressure and using the vacuum mixing process, evaporation can be brought about both of the water and the alcohol or both together (azeotropically in the case of isopropanol). This process can also be repeated a number of times.

Specific features of the present invention include the following. The pre-reaction product between the organic acid and the carbonate is at a temperature of 30° to 40° C. when added to the crystals of organic acid. The pre-reaction product should have a concentration such that it remains a clear solution until its reaction with the crystals of organic acid.

The pre-reaction product may contain a salt which is non-reactive toward the organic acid. Suitable non-reactive salts include calcium lactate, calcium levulate, and calcium gluconate, particularly calcium heptagluconate. The non-reactive salt may be present in an amount of from 5 to 30% by weight of the pre-reaction product.

When starch is added to the pre-reaction product it is added in anhydrous form to the extent of 2 to 8% by weight of the pre-reaction product.

The particularly preferred embodiment of the invention, in which on the one hand anhydrous starch and on the other anhydrous calcium salts of the claimed type are added to the at least one calcium carbonate-containing coating has the particular advantage that the calcium concentration of the effervescent granular material can be increased without impairing the dissolution rate and whilst in fact drastically increasing the same, accompanied by a further significant improvement to the keeping qualities of the effervescent granular material. Due to the fact that these additives are used in anhydrous manner, they act as a desiccant during the storing of the granules or effervescent tablets, in that they prevent the starting off of a water-releasing chain reaction between the calcium carbonate and the citric acid, which would lead to the premature ageing and rendering unusable of the effervescent granules or tablets. The starch also acts as a disintegrating agent for the additional calcium salts, which are otherwise difficultly soluble and/or non-reactive with the edible organic acid, so that said salts are particularly rapidly distributed in the water utilizing the mechanical disintegrating action on dissolving the effervescent granular material. Effervescent granular materials prepared according to this preferred embodiment are particularly suitable as an incident product, the dissolving time being approximately 20 to 30 seconds at approximately 5° C., compared with the calcium carbonate product, which unacceptably requires several minutes for dissolving at such low temperatures.

It is particularly important for the invention that the starch is used in the completely anhydrous state, because only then is a corresponding quasi-mechanical disintegrating action ensured, which guarantees the aforementioned short dissolving times. Effervescent granular materials prepared according to the inventive process are so stable that they can be stored in an open bottle due to the synergistically obtained (desiccant characteristics) of the anhydrous starch on the one hand and the anhydrous calcium salts which are difficultly soluble or non-reactive with the edible organic acid on the other.

It must be borne in mind that the inventive concept of using the prereacted "buffer granulating solutions" although preferably used in the vacuum mixing process of the known type also leads to the important advantages referred to in the case of "open air granulation", i.e. granulation without using vacuum mixing machines, granulation then taking place e.g. in mixers or the like on an industrial scale and final drying can take place by means of belt driers or the like. As claimed, it is also possible according to the invention to prepare isotonic and hypertonic effervescent granular materials, which are characterized in that they can be mixed up to a ratio of approximately 1:5 with instant sugar and as a result of the density of the granular material and its surprisingly high local effervescence capacity, they are able to whirl through up to five times the quantity of instant sugar and simultaneously dissolve the same. As a result, it is possible to produce instant soft drinks which, like conventional soft drinks, contain 8 to 10% by weight of sugar, but also the necessary quantity of citric acid, mineral acids, such as calcium, magnesium, sodium and potassium, obviously together with flavouring additives. Such instant products differ in an extremely advantageous manner from the hitherto known similar instant products, which only very slowly dissolve in water accompanied by stirring and which have a relatively flat taste.

DETAILED DESCRIPTION OF THE PREFERRED EMBODIMENTS

Further features and advantages of the invention can be gathered from the following description of non-limitative embodiments.

EXAMPLE 1

270 parts by weight of crystalline citric acid are heated to 60° C. in the vacuum boiler or tank, e.g. in a vacuum mixing machine of the type described in Austrian patent 37 61 47. A solution consisting of 5.7 parts by weight of distilled water and 3.7 parts by weight of citric acid dissolved therein is prepared outside the vacuum tank. This solution is stirred in a high speed stirrer, 0.75 parts by weight of calcium carbonate being introduced and reacted with the citric acid. The solution is heated to 35° C.

At the end of the reaction process, the thus prepared prereaction solution at 35° C. is sucked on to the evacuated citric acid in the vacuum tank and distributed or dispersed on the surface of the acid crystals by oscillatory stirring. Following this dispersion and still in vacuo, 130 parts by weight of calcium carbonate and 30 parts by weight of pulverized citric acid are introduced and dispersed on the surface of the citric acid crystals. Only a slight reaction occurs, because a prereaction had already been performed outside the vacuum mixing machine. However, the reaction is still sufficient to permit, following dispersion, a further quantity of 30 parts by weight of citric acid and 60 parts by weight of calcium carbonate to be introduced and reacted.

The added partially neutralized citric acid prereaction solution obviously continues to react and forms further reaction water by splitting off giving a highly concentrated solution of calcium citrates as a binder. Prior to the evaporation of the water and for stopping coating formation, 9 parts by weight of isopropanol are added and as a result of this alcohol addition, the calcium salts are precipitated from the highly concentrated, applied and further formed solution and the water is taken up in the alcohol. Without this step, the water would have a very low vapour pressure in the concentrated solution, or in other words a boiling point of approximately 180° C., so that removal in vacuo would be time consuming. Due to the addition of the alcohol, the salt is precipitated, the water taken up by the alcohol and can be removed azeotropically together therewith. This leads to substantially anhydrous binder coatings with a very limited residual moisture content and therefore very good stability characteristics of the thus prepared effervescent granules.

The above process can be repeated a number of times, the concentrations of the solution or prereaction solution used naturally being variable within wide limits. Thus, e.g. if "finished" calcium salts, such as calcium lactate or calcium heptagluconate are introduced into a coating stage, then these already neutral salts act as reaction reducing agents, so that it is possible to work with less strongly neutralized or prereacted solutions. However, on incorporating starch, it can be advantageous to use highly concentrated solutions to prevent the introduction of residual moisture into the starch. Here again, a subsequent treatment with alcohol, preferably isopropanol and also in vacuo, represents a very advantageous possibility for removing residual moisture from the starch, whilst correspondingly favourably influencing the stability of the thus prepared effervescent granules.

EXAMPLE 2

The procedure according to the invention is particularly advantageous when handling hygroscopically difficult potassium salts. For this purpose 250 parts by weight of crystalline citric acid with a particle size of 0.4 to 0.6 mm are mixed with a solution of 20 parts by weight of citric acid in 15 parts by weight of water, accompanied by the addition of 20 parts by weight of potassium bicarbonate and, as in example 1, the prereaction solution is prepared by dissolving with a high speed stirrer. Subsequently 210 parts by weight of pulverized potassium bicarbonate are added. The prereaction solution essentially comprising potassium dicitrate acts as a binder and buffer between the citric acid and potassium bicarbonate. A violent reaction cannot occur, because potassium dicitrate reacts very slowly and inertly with the potassium bicarbonate. Thus, not only can a granulation, i.e. a build-up of a uniform free-flowing structure take place, but it is also ensured that a passivating coating is incorporated between the citric acid crystals and the very hygroscopic potassium bicarbonate. It is advisable and advantageous in this procedure to add a larger alcohol quantity, preferably 3 to 4 times the previously used water quantity following one or two coating procedures of the aforementioned type, in order to anhydrously precipitate the alcohol-insoluble potassium salts and to remove the water serving as the solvent with alcohol and in the case of isopropanol particularly advantageously in an azeotropic manner.

This procedure leads to excellent free-flowing granules, which can be moulded or compressed to give extremely hard effervescent tablets, which have a greatly reduced sensitivity to atmospheric humidity, because potassium dicitrate is also in a position to incorporate water of crystallization, unlike in the case of potassium monocitrate. A similar possibility exists in the case of potassium tricitrate and then, the prereaction solution does not contain 20 parts of weight of potassium bicarbonate, as described hereinbefore, but 30 parts by weight thereof. Thus, in this case granulation takes place with a solution of potassium tricitrate, which is once again anhydrously precipitated by alcohol and a passivating coating forms between the individual reactants, i.e. the acid crystals and the first coating or two successive coatings.

Experience has, however, shown that potassium dicitrate is more advantageous, because the adhesive power of this salt, which subsequently probably constitutes a mixture of potassium mono, di and tri-citrates within the scope of the reaction ensures much better binding characteristics than a particular potassium tricitrate, to give only one example.

EXAMPLE 3

The procedure of example 2 is adopted, but additionally a magnesium oxide coating is applied. For this purpose, 90 parts by weight of crystalline citric acid are mixed with the potassium dicitrate solution. The prereaction solution prepared in example 2 is then distributed or dispersed on the citric acid crystals by mixing and then 20 parts by weight of potassium bicarbonate are applied. Further prereaction solution is then introduced, following the anchoring of 11 parts by weight of magnesium oxide as the intermediate coating. Subsequently further prereaction solution and 25 parts by weight of potassium bicarbonate are applied, so as to obtain a terminating coating, before final drying takes place accompanied by stirring.

The procedure according to the invention avoids the necessity, even when no vacuum mixing process is used, i.e. granulation takes place under atmospheric conditions, of carrying out prolonged heat treatment of the effervescent tablets and also granules following the wet moulding or compression of the still moist granules. During such a heat treatment, such as is conventional in the prior art, there is a partial evaporation of the water and reactions of the aforementioned type, such as are performed in vacuo according to the invention take place in the end product, obviously without it then being possible to remove the water of crystallization. In addition, the constituents added in the prior are procedure and particularly vitamins, but also flavours, are destroyed by the moisture and acid or strong alkaline reactants, so that such a procedure is unsuitable for sensitive active substances. This leads to an important advantage of the inventive procedure compared with the process called "curing" and which is particularly described in US literature, namely the treatment of the wet-moulded tablets by subsequent final drying by means of prolonged heat treatment (e.g. Herbert A. Liebermann and Leon Lachmann, "Pharmaceutical dosage forms - tablets", vol. 1, pp 232-243).

The features of the invention disclosed in the above description and the claims can be essential to the realization of the different embodiments of the invention, either singly, or also in random combination.

What is claimed is:

1. A process for the preparation of an effervescent granular material containing at least one solid, crystalline edible organic acid and at least one carbonate of an alkali metal or an alkaline earth metal which splits off $CO_2$ upon reacting with said organic acid in aqueous solution which comprises:

pre-reacting a portion of said organic acid and said carbonate in solution in water and/or alcohol to form a pre-reaction product, adding said pre-reaction product to an additional portion of said organic acid in crystalline form with thorough mixing to form a first coating by reaction with said organic acid crystals and liberation of the resulting water of crystallization, applying at least one additional coating including said organic acid and said carbonate onto the organic acid crystals with said first coating adhering thereto, and terminating the reaction after the last coating has been applied by treating the coated crystals with an alcohol in which the salt formed between said organic acid and said alkali metal or alkaline earth metal is insoluble.

2. A process according to claim 1 wherein after application of said additional coating, there is at least one additional wetting of the coated crystals with a pre-reaction product of said organic acid and said carbonate.

3. A process according to claim 1 wherein said pre-reaction product is at a temperature of 30° to 40° C. when added to the crystals of said organic acid.

4. A process according to claim 1 wherein said pre-reaction product has a concentration such that it remains a clear solution until its reaction with the crystals of said organic acid.

5. A process according to claim 1 wherein said organic acid is citric acid.

6. A process according to claim 1 wherein said alcohol is ispropanol.

7. A process according to claim 1 wherein said pre-reaction product also contains a salt which is non-reactive toward said organic acid.

8. A process according to claim 7 wherein the non-reactive salt is calcium lactate.

9. A process according to claim 7 wherein the non-reactive salt is calcium levulate.

10. A process according to claim 7 in which the non-reactive salt is a calcium gluconate.

11. A process according to claim 10 wherein said non-reactive salt is calcium heptagluconate.

12. A process according to claim 1 wherein said pre-reaction product also contains starch.

13. A process according to claim 7 wherein said salt is a calcium salt in an amount of from 5 to 30% by weight of said pre-reaction product.

14. A process according to claim 12 wherein said pre-reaction product contains from 2 to 8% by weight of anhydrous starch.

15. A process according to claim 11, wherein at least one coating compound other than said pre-reaction product with a content of starch and/or an alkali metal and/or an alkaline earth metal compound, e.g., a metal salt or oxide, like magnesium oxide, which is difficultly soluble and/or non-reactive with the edible organic acid is used.

16. A process according to claim 15, wherein the non-reactive salt used is calcium lactate.

17. A process according to claim 15, wherein the non-reactive salt used is calcium levulate.

18. A process according to claim 15, wherein the non-reactive salt used is calcium gluconate.

19. A process according to claim 15, wherein the non-reactive used is calcium heptagluconate.

20. A process according to claim 15, wherein the particular coating is prepared with a content of 5 to 30% by weight of non-reactive calcium salt, based on the particular alkali metal and/or alkaline earth metal carbonate content.

21. A process according to claim 15, wherein the particular starch-containing coating is prepared with a content of 2 to 8% by weight of anhydrous starch, based on the particular alkali metal and/or alkaline earth metal carbonate compound.

* * * * *